US009132160B2

(12) United States Patent
Yang et al.

(10) Patent No.: US 9,132,160 B2
(45) Date of Patent: Sep. 15, 2015

(54) COMPOSITION FOR PREVENTING AND/OR ALLEVIATING HANGOVER COMPRISING EXTRACTS OF SOPHORA FLAVESCENS

(71) Applicant: KOREA INSTITUTE OF SCIENCE AND TECHNOLOGY, Seoul (KR)

(72) Inventors: Hyun Ok Yang, Seoul (KR); Hak Cheol Kwon, Seoul (KR); Joon Ki Kim, Gunpo (KR); Jin Wook Cha, Incheon (KR); Young-Joo Kim, Seoul (KR); Jungyeob Ham, Gangneung (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 318 days.

(21) Appl. No.: 13/661,205

(22) Filed: Oct. 26, 2012

(65) Prior Publication Data
US 2014/0120188 A1    May 1, 2014

(30) Foreign Application Priority Data
Oct. 31, 2011    (KR) .................. 10-2011-0112394

(51) Int. Cl.
*A61K 36/00*    (2006.01)
*A61K 36/489*    (2006.01)

(52) U.S. Cl.
CPC .................. *A61K 36/489* (2013.01)

(58) Field of Classification Search
None
See application file for complete search history.

(56) References Cited

U.S. PATENT DOCUMENTS

2003/0190375 A1    10/2003    Erdelmeier et al.

FOREIGN PATENT DOCUMENTS

| CN | 1438893 | A | | 8/2003 |
|---|---|---|---|---|
| CN | 101878835 | A | * | 11/2010 |
| KR | 10-0768830 | | | 10/2007 |
| WO | 2007/120007 | A1 | | 10/2007 |

OTHER PUBLICATIONS

Kwon et al., "Effects of Plant Vinegar Extract on the Reduction of Blood Concentration of Alcohol and Acetaldehyde in Alcohol Administered Rats", The Journal of Applied Pharmacology, 13, 107-112(2005).
Park, S. J. et al, "Neuroprotective effects of an alkaloid-free ethyl acetate extract from the root of *Sophora flavescens* Ait. Against focal cerebral ischemia in rats", Phytomedicine (2009), 16(11), 1042-1051.
Kim, J.-H. et al, "Glycosidase Inhibitory Flavonoids from *Sophora flavescens*", Biological & Pharmaceutical Bulletin (2006), 29(2), 302-5.
Jin et al., "Anti-inflammatory and anti-arthritic activity of total flavonoids of the roots of *Sophora flavescens*", Journal of Ethnopharmacology, 2010, 123, 589.
Zheng et al., "Antimicrobial Activity of the Flavonoids in *Sophora flavescens* Extraction", Wuhan Daxue Xuebao, Lixueban, 2008, 54, 439.
De Naeyer et al., "Estrogenic and Anticarcinogenic Properties of Kurarinone, a Lavandulyl Flavanone from the Roots of *Sophora flavescens*", Journal of Natural Products, 2004, 67, 1829.
Shigenobu Okuda et al. Studies on Lupin Alkaloids. I. The Minor Alkaloids of Japanese *Sophora flavescens*. Chem Pharm. Bull. 13(4). pp. 482-487. (1965).
Korean Office Action for corresponding Korean Application 10-2011-0112394; dated May 16, 2013.
Extended European Search Report mailed Jan. 18, 2013 in corresponding European Patent Application No. 12190610.1.
John M. Luk et al., "Traditional Chinese herbal medicines for treatment of liver fibrosis and cancer: from laboratory discovery to clinical evaluation", Liver International ISSN 1478-3223, 2007, pp. 879-890.
Database WPI, Week 201114, Thomson Scientific, London, GB, AN 2010-Q13057 X9002689871, 2 pp.
Eun Ju Choi et al., "Four Flavonoids from *Enchinosophora koreenis* and their effects on Alcohol Metabolizing Enzymes", Archives of Pharmacal Research, vol. 32, No. 6, pp. 851-855, 2009, DOI 10.1007/s12272-009-1606-2.
Xiao-Xia Lü et al., "Alcohol and Disease", ISBN 978-7-5607-3363-0, pp. 119-120 (with a cover page), 2007.
Manki Komatsu et al., "Studies on the Constituents of *Sophora* Species. XIII.[1)] Constituents of the Aerial Parts of *Sophora tomentosa* L. (2)", Pharmaceutical Society of Japan, 1978, vol. 26, No. 12, pp. 3863-3870.
Kim S, A biotinylated flavonoid compound as a tyrosinase inhibitors in *Sophora* [English]/ Kim s . . . //Biol Pharm Bull.2003, 26 (9) -1348 ~1350.
Eun Ju Choi et al.,Four Flavonoids from *Echinosophora koreensis* and their Effects on Alcohol Metabolizing Enzymes, Archives of Pharmacal Research , 2009, vol. 32, No. 6, 851-855.
Lei Zhang et al.,Characterization of flavonoids in the extract of *Sophora flavescens* Ait.By high performance liquid chromatography coupled with diode-array detector and electrospray ionization mass spectrometry, Journal of Pharmaceutical and Biomedical Analysis, Apr. 24, 2007,vol. 44, 1019-1028.

* cited by examiner

*Primary Examiner* — Qiuwen Mi
(74) *Attorney, Agent, or Firm* — Goldilocks Zone IP Law (57) ABSTRACT

A method of preventing or alleviating alcohol hangover, which comprises administering one or more selected from the group consisting of *Sophora flavescens* extracts, dried products of the extracts, and concentrates of the extracts to a subject in need of preventing or alleviating alcohol hangover is provided.

6 Claims, 6 Drawing Sheets

Fig. 1
Ethanol Degradation Test

COMPOSITION FOR PREVENTING AND/OR ALLEVIATING HANGOVER COMPRISING EXTRACTS OF SOPHORA FLAVESCENS

CROSS-REFERENCE TO RELATED APPLICATIONS

This application claims the benefit under 35 U.S.C. Section 119 of Korean Application No. 10-2011-0112394 filed on Oct. 31, 2011 in the Korean Intellectual Property Office, which is hereby incorporated by reference in its entirety into this application.

BACKGROUND OF THE INVENTION (a) Field of the Invention

The present invention provides uses of *Sophora flavescens* extracts or fractions prepared from the extracts for activating alcohol dehydrogenase (ADH) and acetaldehyde dehydrogenase (ALDH), removing blood alcohol, and/or preventing and/or alleviating alcohol hangover.

(b) Description of the Related Art

Due to frequent and excessive drinking under the drinking culture of our country, many people are very interested in medicines or drinks that can remove hangover. Hangover includes the symptoms such as headache, diarrhea, anorexia, nausea, emesis, chill, cold sweating, etc. shown after drinking, and also includes deterioration of gnosia and exercise capacity, hematological change and hormonal change as the objective symptoms. It has been known that hangover is caused by dehydration, toxicity of alcohol and alcohol metabolites (acetaldehyde, formaldehyde, acetone, etc.), lack of nutrients (lack of blood glucose, vitamin or mineral) due to the dyspepsia, etc. Degree of hangover is very diverse depending on the individual variations due to the heredity and environmental conditions (nutritional status, exercise status, degree of dehydration, health status).

After drinking, alcohol is metabolized via three routes. It is metabolized by alcohol dehydrogenase and acetaldehyde dehydrogenase which exist in the gastrointestinal tract or the liver when the ethanol concentration is low or by microsomal ethanol oxidizing system (MEOS) which exists in the endoplasmic reticulum when the ethanol concentration is high to acetaldehyde and acetic acid, and then is finally decomposed by the action of catalase, etc. which exist in the peroxisome to carbon dioxide ($CO_2$) and water ($H_2O$). If an adequate amount of alcohol is taken, the above stated metabolic system properly works to prevent the various symptoms caused by alcohol. However, if a lot of alcohol is taken, the equilibrium of metabolic system may be disrupted to disturb the homeostasis, resulting in headache or pressure in the head, reduced attention, brash, dyspepsia, etc. in the short term and dyshepatia in the long term.

For the alleviation of hangover symptoms, currently there are several commercial drink products such as: Condition by CJ Corporation made of extracts from cili, hedysarum, lotus seed, rice germ, raisin tree, etc.; Morning Care by Dong—A Pharmaceutical Co., Ltd. with main ingredients from fermented rice embryo and soybean extracts and milk thistle extract powder; Dawn 808 by Glami Co., Ltd. with extracts from alder tree, rowan tree.

*Sophora flavescens* Aiton, commonly called light yellow *sophora*, is a perennial plant that belongs to the Leguminosae of Dicotyledon family. It grows in the sunny green field. It is green and 80-100 cm tall, and has a black hue when it is young. Stems are straight and its oddly pinnate leaves are arranged crisscrossed. There are 15-40 leaflets. Each leaflet is 2-4 cm long, 7-15 mm wide, and in the shape of a long oval or long egg. The petiole is long and its border is smooth. Between June and August, flower stems sprout from the end of branches growing 20 cm long and produce in a raceme light yellow flowers in the shape of butterfly. The length of flower is 15-18 mm. The calyx is in the shape of a keg and has hairy exterior and five thin split tips. The fruit is a legume in the shape of beads. It has a short haulm and is 7-8 cm long and ripens between September and October. Its dried root is called bitter ginseng in oriental medicine. In the Korean Pharmacopoeia, it is described as herbal medicine with a bitter taste and for its ginseng effects it is prescribed for dyspepsia, neuralgia, hepatitis, jaundice, hemorrhoids, etc. Also, in folk medicine, stems and leaves are decocted and used as an insecticide. *Sophora subprostrata* Chun et T. Chen is a plant that belongs to the same genus and looks very similar to the *Sophora flavescens* Aiton. It inhabits in Korea, Japan, China, Siberia, etc.

*Sophora flavescens*'s main ingredients are flavonoids and alkaloids. Research studies have reported its neurtroprotective actions (Park, S.-J. et al. *Phytomedicine* (2009), 16(11), 1042-1051) and glucosidase inhibitory effect (Kim, J.-H. et al, *Biological & Pharmaceutical bulletin* (2006), 29(2), 302-5). Also, studies with flavonoid fraction of *Sophora flavescens* reported anti-inflammatory and arthritic effect (Jin et al, Journal of ethnopharmacology, 2010, 123, 589), antimicrobial effect (Zheng et al, Wuhan DaxueXuebao, *Lixueban*, 2008, 54, 439), and estrogen mimicking and anticancer activities (De Naeyer et al, Journal of natural products, 2004, 67, 1829).

Including the above researches, a variety of physiological activities of *Sophora flavescens* extracts and compounds separated therefrom have been reported. However, there is no report on the physiological activities of *Sophora flavescens* or extracts thereof related to enzymes for alcohol metabolism and alleviation of hangover.

SUMMARY OF THE INVENTION

The present inventors have found that the *Sophora flavescens* extract reduces blood alcohol level, and that fractions prepared from the *Sophora flavescens* extract, such as an ethyl acetate fraction and a dichloromethane fraction, also increase activities of alcohol dehydrogenase and acetaldehyde dehydrogenase to facilitate alcohol metabolism and alleviate hangover, to complete the present invention.

Therefore, an embodiment provides a composition for preventing and/or alleviating hangover, which comprises one or more active ingredients selected from the group consisting of *Sophora flavescens* extracts, dried products of said extracts and concentrates of said extracts.

Another embodiment provides a method of preventing and/or alleviating hangover, comprising administering one or more active ingredients selected from the group consisting of *Sophora flavescens* extracts, dried products of said extracts and concentrates of said extracts to a subject in need of preventing and/or alleviating hangover.

Another embodiment provides a use of one or more active ingredients selected from the group consisting of *Sophora flavescens* extracts, dried products of said extracts and concentrates of said extracts in preventing and/or alleviating hangover or in preparing a composition for preventing and/or alleviating hangover.

DETAILED DESCRIPTION OF THE EMBODIMENTS

The present inventors have confirmed that the extract of the herbal medicine *Sophora flavescens*, which is registered in the Korean Pharmacopoeia and is traditionally used as food for the medicinal use, has the effect of facilitating decrease of blood alcohol concentration in rats injected by alcohol and the effect of decreasing the glutamate-oxaloacetate transaminase (GOT) which is a measurement factor for liver injury due to alcohol. They also have demonstrated that the ethyl acetate fraction and the dichloromethane fraction derived from the *Sophora flavescens* extract exhibit the superior effects of increasing activities of alcohol dehydrogenase (ADH) and acetaldehyde dehydrogenase (ALDH), both of which play an important role for alcohol metabolism in the body, and thus facilitating alcohol metabolism in the body to decrease blood alcohol and acetaldehyde concentrations increased through the ingestion of alcoholic liquors. Thus, the present invention suggests that the *Sophora flavescens* extracts or the fractions prepared from the extracts may be effectively used for the prevention and/or alleviation of alcohol hangover.

An embodiment of the present invention provides a pharmaceutical composition for preventing and/or alleviating alcohol hangover, which comprises one or more active ingredients selected from the group consisting of *Sophora flavescens* extracts, dried products of said extracts and concentrates of said extracts.

Another embodiment provides a method of preventing or alleviating alcohol hangover, comprising administering a pharmaceutically effective amount of one or more selected from the group consisting of *Sophora flavescens* extracts, dried products of the extracts, and concentrates of the extracts to a subject in need of preventing or alleviating alcohol hangover. The method may further comprise a step of identifying a subject in need of preventing or alleviating alcohol hangover, prior to the administering step. The subject may be a mammal, for example a human.

Still another embodiment provides a use of one or more selected from the group consisting of *Sophora flavescens* extracts, dried products of the extracts, and concentrates of the extracts in preparing a pharmaceutical composition for preventing or alleviating alcohol hangover.

The term '*Sophora flavescens* extract' as used herein comprises all the crude extracts and fractions obtained by solvent fractionation of the extracts. The extracted part of *Sophora flavescens* may be a whole plant, a root, a leaf, or a stem, preferably a root (such as a dried root).

The term 'pharmaceutically effective amount' as used herein may refer to an amount at which one or more selected from the group consisting of the *Sophora flavescens* extracts, dried products of the extracts, and concentrates of the extracts may exhibit the activity of preventing or alleviating alcohol hangover.

Thus, the *Sophora flavescens* extract as the active ingredient of the pharmaceutical composition according to the present invention may be one or more selected from the group consisting of

*Sophora flavescens* crude extracts obtained by extracting *Sophora flavescens* using one or more extraction solvents selected from the group consisting of water, straight-chain or branched $C_1$-$C_4$-alcohol, dichloromethane, ethyl acetate, acetone, and the like; and

*Sophora flavescens* fractions obtained through the solvent fractionation by adding one or more fractionation solvents selected from the group consisting of hexane, chloroform, ether, dichloromethane, ethyl acetate, butanol, water, and the like to the *Sophora flavescens* crude extract, for achieving more excellent effect of alleviating hangover.

*Sophora flavescens* may be those grown wild or cultivated. Particularly, *Sophora flavescens* refers to the root thereof. However, the whole plant including the root as well as the root only may be used for preparing the *Sophora flavescens* extracts, with or without being dried.

The amount of extraction solvent for obtaining the *Sophora flavescens* crude extract, for the sufficient and effective extraction of the active ingredients, may be 1 to 30 times by volume (for example, 1 to 30 mL of solvent is used for 1 g of *Sophora flavescens*), preferably 2 to 10 times by volume, with respect to the weight of *Sophora flavescens*.

The extraction time may range from 1 to 12 h, preferably from 3 to 6 h, for the sufficient extraction of the active ingredient, but not limited thereto. The extraction temperature may range from room temperature to the boiling point of the extraction solvent for the sufficient extraction of the active ingredient, but not limited thereto.

The extraction for obtaining the extract of the present invention may be carried out in accordance with the extraction methods typically known in the art to which the present invention pertains. Specifically, any typical extraction methods such as enfleurage, extraction by heat, extraction by ultrasonic waves, filtration, pressure extraction, reflux extraction, supercritical fluid extraction, electric extraction, etc. may be used.

The *Sophora flavescens* fractions mean those obtained by the fractionation wherein a fractionation solvent is added to the *Sophora flavescens* crude extract. For example, they may be obtained by a method where the *Sophora flavescens* crude extract as obtained above is suspended in water and the resulting suspension is fractionated by adding one or more fractionation solvents selected from the group consisting of hexane, chloroform, ether, dichloromethane, ethyl acetate, butanol, etc. in the same volume as water thereto; and/or the *Sophora flavescens* crude extract as obtained above is fractionated by adding one or more fractionation solvents selected from the group consisting of hexane, chloroform, ether, dichloromethane, ethyl acetate, butanol, and water.

More specifically, the *Sophora flavescens* fractions may be obtained by suspending the *Sophora flavescens* crude extract as obtained above in water of 5 to 40 times by volume, preferably 10 to 30 times by volume, with respect to the solid content (dry weight) of the crude extract and by adding one or more fractionation solvents selected from the group consisting of hexane, chloroform, ether, dichloromethane, ethyl acetate, butanol, etc. in the same volume as water to the suspension thus obtained to fractionate the suspension. In another embodiment, the fractions may be obtained by adding one or more fractionation solvents selected from the group consisting of hexane, chloroform, ether, dichloromethane, ethyl acetate, butanol, water, etc. of 1 to 30 times by volume, preferably 2 to 10 times by volume, with respect to the solid content (dry weight) of the crude extract to the *Sophora flavescens* crude extract as obtained above to fractionate it.

When two or more solvents are used as the fractionation solvent, the *Sophora flavescens* fractions may be the respective solvent fractions obtained by carrying out the solvent fractionations using the two or more fractionation solvents according to the above stated order.

Also, if necessary, filtration and/or concentration and/or freeze-drying methods known in the art may be additionally applied after the above extraction and/or fractionation. Dried product or concentrate of the extract (crude extract and/or fraction) used in the present invention refers to those dried or concentrated according to the known methods as described above.

In concrete examples, *Sophora flavescens* is extracted from a solvent mixture of alcohol and water in the ratio of 8:2 by volume, the extract thus prepared is orally administered to rats and then alcohol is orally administered to the same rats.

As a result, it has been confirmed that the blood alcohol concentration (see Experiment 1) and the GOT (Glutamate-Oxaloacetate Transaminase) value (see Experiment 2) are decreased. In another experiment, the dichloromethane, ethyl acetate, butanol and water fractions prepared from the *Sophora flavescens* extract are evaluated for their effects on the alcohol dehydrogenase and acetaldehyde dehydrogenase. As a result, it has been identified that the ethyl acetate fraction shows the most superior effect in increasing the activities of alcohol dehydrogenase (see Experiment 3) and acetaldehyde dehydrogenase (see Experiment 4). In another experiment, the *Sophora flavescens* extract used in Experiment 1 is orally administered to rats and then alcohol is orally administered to the same rats. As a result, it has been identified that the extract mitigates deterioration of the exercise capacity on the rotarod due to the alcohol ingestion (see Experiment 5) and that the extract has the effect of sleep-wake (see Experiment 6).

The *Sophora flavescens* extract (crude extract and/or fraction) as the active ingredient in the composition according to the present invention may be contained in the amount suitably adjusted depending on the form and object of use, condition of patient, type and severity of symptom, etc., i.e., 0.001 to 99.9% by weight, preferably 0.1 to 50% by weight, with respect to the solid content, but not limited thereto. The 'solid content' refers to the weight of ingredient after removal of the solvent from the crude extract or fraction.

The pharmaceutical composition of the present invention may be administered via various routes to mammals including the human being. It may be administered by any manner typically used in the art, including oral or rectal administration, or intravenous, intramuscular, subcutaneous, intrauterine subdural or intracerebroventricular injection. The pharmaceutical composition of the present invention may be formulated by conventional methods to oral preparations such as powder, granule, tablet, capsule, suspension, emulsion, syrup, aerosol, etc., parenteral preparations in the form of transdermal agent, suppository, sterile injection solution, etc.

The present composition for alleviating alcohol hangover may comprise pharmaceutically appropriate and physiologically acceptable adjuvants such as carrier, excipient, diluent, etc. in addition to the *Sophora flavescens* extract (crude extract and/or fraction). As the carrier, excipient, diluent, etc. that can be contained in the pharmaceutical composition of the present invention, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxy benzoate, propyl hydroxy benzoate, talc, magnesium stearate and mineral oil may be mentioned. In the case of formulation, the typically used diluents or excipients such as fillers, extenders, binders, wetting agents, disintegrating agents, surfactants, etc. can be used. The solid preparations for oral administration may include tablet, pill, powder, granule, capsule, etc., and such solid preparations may be compounded by mixing the *Sophora flavescens* extract or a fraction prepared therefrom with at least one excipients selected from starch, calcium carbonate, sucrose, lactose, gelatin, etc. Beside the simple excipients, lubricants such as magnesium stearate, talc, etc. are also used. The liquid preparations for oral use include suspension, liquid for internal use, emulsion, syrup, etc., and they may comprise various excipients, such as for example, wetting agent, sweetener, aromatic, preservative, etc. beside water and liquid paraffin as the simple diluent frequently used. The parenteral preparations include sterile aqueous solution, non-aqueous solution, suspension, emulsion, freeze-dried preparation, suppository, and transdermal preparation, etc. As the non-aqueous solvent or suspending agent, propylene glycol, polyethylene glycol, a vegetable oil such as olive oil, an injectable ester such as ethyl oleate, etc. may be used. As the base for suppository, witepsol, macrogol, tween 61, cacao butter, laurin butter, glycerogelatin, etc. may be used.

The pharmaceutical composition of the present invention may be administered alone to the human being. However, taking into account the conventional manner of administration and the standard pharmaceutical practice, it may be administered after being mixed with the selected pharmaceutical carriers. For example, the pharmaceutical composition of the present invention may be orally, buccally or sublingually administered in the form of a tablet containing starch or lactose, in the form of a capsule of the composition alone or containing some excipients, or in the form of an elixir or suspension containing some chemicals which provide taste or color. Such liquid preparations may be formulated together with the pharmaceutically acceptable additives such as a suspending agent (e.g., glycerides mixtures such as semi-synthetic glycerides including methyl cellulose or witepsol, or apricot kernel oil with PEG-6 ester, or PEG-8 with caprylic/capric glyceride).

In another aspect, the present invention provides a food composition for preventing and/or alleviating hangover, which comprises one or more selected from the group consisting of the *Sophora flavescens* extracts, dried products of said extracts and concentrates of said extracts. As stated above, the *Sophora flavescens* extracts are one or more selected from the group consisting of the *Sophora flavescens* crude extracts and the fractions obtained by fractionation from the crude extracts. The *Sophora flavescens* crude extracts and fractions therefrom are as explained above.

The food as used herein means natural or processed products containing one or more nutrients. Under the conventional meaning, it comprises food, health supplement, drink, food additive and drink additive of every kind. And, the food composition means the combinations of materials for preparing the food. As examples of the food, food, drink, gum, tea, functional food, etc. of every kind may be mentioned. In addition, the food as used herein comprises special dietary food (e.g., milk formula, infant formula, etc.), processed meat product, fish product, tofu, jellies, noodles (e.g., ramen, noodle, etc.), health supplement, confectionaries (e.g., snacks), other processed food, drink, functional drink for health (e.g., drink for alleviating hangover, etc.) and other health supplements, but is not limited thereto. Said health supplement, drink, food additive or drink additive may be prepared according to the conventional methods.

The content of the *Sophora flavescens* extract or fraction in the above food composition may be suitably adjusted depending on the form, object, etc. of use of the food, i.e., 0.00001 to 99.9% by weight, preferably 0.001 to 50% by weight, with respect to the solid content, but is not limited thereto.

In another aspect, there is provided a process for preparing the *Sophora flavescens* extract which is excellent in the activation of alcohol metabolism and/or the alleviation of hangover. This process may comprise the steps of 1) extracting *Sophora flavescens* with one or more solvents selected from the group consisting of water, straight-chain or branched $C_1$-$C_4$-alcohol, dichloromethane, ethyl acetate, acetone, etc. to give the *Sophora flavescens* crude extract; and 2) fractionating the *Sophora flavescens* crude extract as obtained above by one or more solvents selected from the group consisting of hexane, chloroform, ether, dichloromethane, ethyl acetate, butanol, water, etc. to give the *Sophora flavescens* fraction.

The above extracting step 1) may be performed by adding a solvent mixture of water and straight-chain or branched $C_1$-$C_4$-alcohol (e.g., ethanol) in the mixing ratio of 1:9 to 5:5 (e.g., about 2:8) by volume, or straight-chain or branched $C_1$-$C_4$-alcohol (e.g., ethanol) to the *Sophora flavescens*.

Also, the extracting step may be performed once, or repeated twice or more, e.g., twice or three times, and the filtrates obtained in each extraction step may be combined to give the *Sophora flavescens* crude extract.

For example, the extracting Step 1) may comprise the steps of 1-1) extracting the dried *Sophora flavescens* with a solvent mixture of water and straight-chain or branched $C_1$-$C_4$-alcohol (e.g., ethanol) in the mixing ratio of 1:9 to 5:5 by volume or with straight-chain or branched $C_1$-$C_4$-alcohol (e.g., ethanol) and filtering to give a filtrate; and 1-2) concentrating the filtrate obtained in Step 1-1) to prepare a concentrate or a dried product of the crude extract.

The extraction may be carried out by using any method known and conventionally used in the art, such as for example, enfleurage, extraction by heat, extraction by ultrasonic waves, filtration, pressure extraction, reflux extraction, supercritical fluid extraction, electric extraction, etc.

In another example, the fractionating Step 2) may comprise the steps of 2-1) suspending the *Sophora flavescens* extract obtained in Step 1) in water of 5 to 40 times by volume, preferably 10 to 30 times by volume, with respect to the solid content (dry weight) of the extract;

2-2) adding one or more solvents selected from the group consisting of hexane, chloroform, ether, dichloromethane, ethyl acetate, butanol, etc. in the same volume as water to the water suspension of the *Sophora flavescens* extract obtained in Step 2-1) and mixing them to fractionate the suspension; and 2-3) concentrating and/or drying the fraction obtained in Step 2-2) to prepare a concentrate or a dried product of the fraction.

In another example, the fractionating Step 2) may comprise the steps of 2-1') adding one or more solvents selected from the group consisting of hexane, chloroform, ether, dichloromethane, ethyl acetate, butanol, water, etc. to the *Sophora flavescens* crude extract obtained in Step 1) in the amount of 1 to 30 times by volume, preferably 5 to 10 times by volume, with respect to the solid content (dry weight) of the crude extract to fractionate the crude extract; and 2-2') concentrating and/or drying the fraction obtained in Step 2-1') to prepare a concentrate or a dried product of the fraction.

The fractionation step of 2-1) or 2-1') may be performed as a single step of using a solvent. It may also be performed as multiple steps of using two or more solvents sequentially according to the above described order wherein the first solvent is used to take up the dissolved portion and the next solvent is added to the remaining portion. The fractionation solvent may be used once, or twice or more, e.g., twice or three times repeatedly, and the fractions obtained in each fractionation step may be combined. When two or more solvents are used in series as the fractionation solvent, the concentrating and/or drying step 2-2) or 2-2') may be subjected to the filtrates which are sequentially taken during the fractionation steps.

As reviewed above, *Sophora flavescens* in the present invention is a traditional herbal medicine which is described in the Korean Pharmacopoeia and has been demonstrated as safe. The *Sophora flavescens* extracts have the effect of facilitating the decrease of blood alcohol concentration in rats administered with alcohol and the effect of decreasing the GOT value. The fractions prepared from the *Sophora flavescens* extracts increase the activities of alcohol dehydrogenase and acetaldehyde dehydrogenase. Thus, the composition of the present invention which comprises the *Sophora flavescens* extract or the fraction prepared from the *Sophora flavescens* extract as the active ingredient can be effectively used for the activation of alcohol metabolism in the body and/or alleviation of hangover.

EXAMPLE

Hereinafter, the present invention will be explained more in detail by the Examples. However, the following Examples are only for the illustration of the present invention and it is not intended that the scope of the present invention is limited in any manner by them.

Example 1

Preparation of the *Sophora flavescens* Extract 0.5 kg of the dried root of *Sophora flavescens* (collected in Yeong-cheon of GyeongBuk) was chopped and introduced into an extraction bottle. This root was soaked in 1.25 L (2.5 times by volume with respect to the weight of sample) of 80% (v/v) aqueous EtOH solution wherein ethanol and water were mixed in the volume ratio of 8:2, extracted under reflux for 3 h and filtered through a filter paper. The extract (filtrate) was concentrated by using a concentrator at 30° C. under reduced pressure until the solvent was completely evaporated to give 75 g of the *Sophora flavescens* crude extract ('KNA32' below).

Example 2

Preparation of Fractions from the *Sophora flavescens* Extract 75 g of the *Sophora flavescens* crude extract KNA32 prepared in <Example 1> was suspended in 1.5 L of water. Then, 1.5 L each of dichloromethane, ethyl acetate and butanol were sequentially added twice, respectively, for the purpose of solvent fractionation. The solvents in the fractions were completely evaporated by using a concentrator at 30° C. under reduced pressure to give 6.4 g of the dichloromethane fraction ('KNA32 MC' below) which had been dissolved in dichloromethane, 10.4 g of the ethyl acetate fraction ('KNA32 EA' below) which had been dissolved in ethyl acetate, 11.5 g of the butanol fraction ('KNA32 BuOH' below) which had been dissolved in butanol and 46.3 g of the water fraction ('KNA32 Water' below) remained.

Experiment 1

Measurement of Efficacy on the Decrease of Blood Alcohol Concentration in Rats Administered with Ethanol In order to measure the efficacy of the *Sophora flavescens* crude extract obtained in <Example 1> on the decrease of blood alcohol concentration, 5 to 6 week-old (140 to 160 g of weight) male SD (Sprague Dawley) rats (Orientbio Inc., Seongnam, Korea) were used as test animals. The rats were fed ad libitum with solid feed and tap water for 1 week, and after this pre-breeding they were subjected to the test.

After 18 hours fast, the control group was orally administered with physiological saline and the test groups were orally administered with suspensions of the *Sophora flavescens* crude extract (KNA32) of <Example 1> in physiological saline in the concentrations of 0.5, 1.0 and 1.5 g/kg/5 ml, respectively. For the comparative groups 1 and 2, two kinds of commercially available drinks for alleviating hangover were selected (Comparative group 1: Heot-gae Condition Power, CJ Cheiljedang; Comparative group 2: Morning Care, Dong—A Pharmaceutical Co., Ltd). The rats of comparative groups were orally administered with these drinks of the selected dose which was calculated based on the recommended dose for the standard weight of an adult (70 kg) (dose concentration: 1.5 ml/kg for Heot-gae Condition Power and Morning Care) after being diluted in physiological saline.

Figure 1:
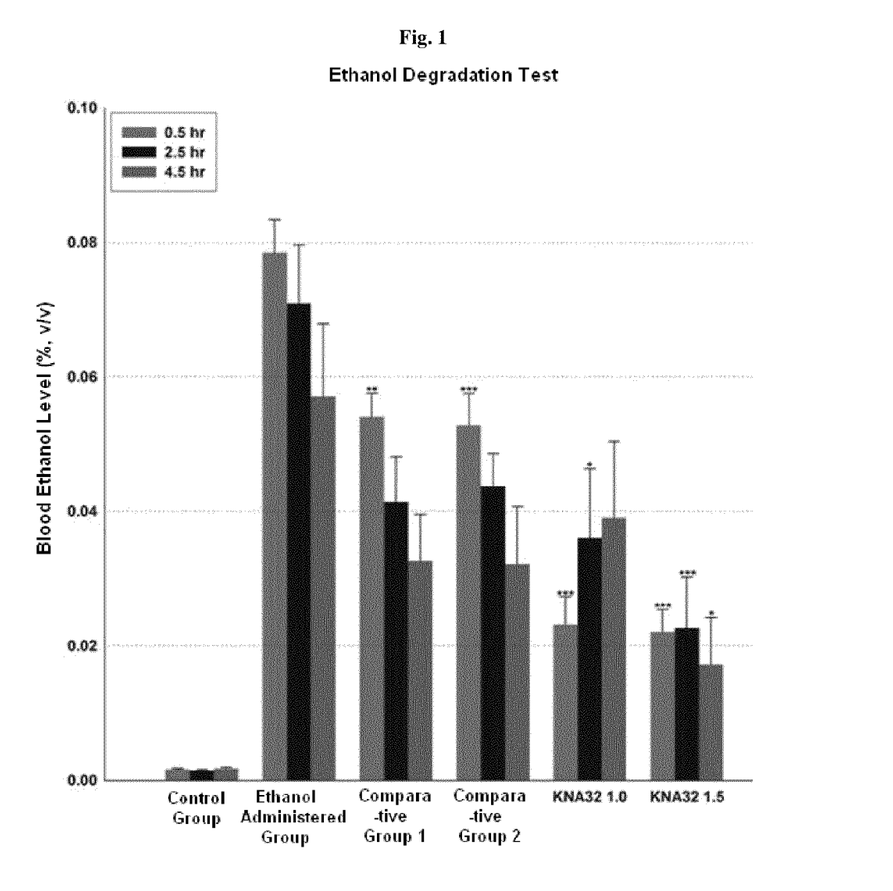
FIG. 1 represents a graph showing the time course change of blood alcohol concentration after administering different doses of the *Sophora flavescens* crude extract according to one example (KNA32) to rats orally administered with alcohol in advance.

After 30 min, the rats of control group, test groups (administered with 0.5, 1.0 and 1.5 g/kg/5 ml of the *Sophora flavescens* crude extract) and comparative groups 1 and 2 were orally administered with alcohol in the concentration of 3 g/kg/10 ml. At 0.5, 2.5 and 4.5 h from the oral administration, blood was collected from the eye socket and heart. The collected blood was centrifuged for 10 min at 4° C., 10,000 rpm to separate the serum. This separated serum was mixed with perchloric acid in the same amount and centrifuged for 10 min at 4° C., 700 g. The supernatant was mixed with 0.5 time by volume of Buffer Solution I (0.4 M KOH, 0.13 M $K_2CO_3$, 0.5 M Tris) and allowed to stand for 30 min at 4° C. This solution was centrifuged for 10 min at 4° C., 700 g to remove proteins. The concentration of ethanol was measured by using an ethanol assay kit (Roche, USA) and the result is represented in FIG. 1 and Table 1.

TABLE 1

| Group | | Blood Ethanol Concentration (%, v/v) | | |
|---|---|---|---|---|
| | | 0.5 h | 2.5 h | 4.5 h |
| Control Group | | 0.0016 | 0.0015 | 0.0017 |
| Ethanol Administration Group | | 0.0784 | 0.0709 | 0.0571 |
| Comparative Group 1 | | 0.0540 | 0.0414 | 0.0327 |
| Comparative Group 2 | | 0.0527 | 0.0437 | 0.0321 |
| KNA32 | 1.0 g/kg | 0.0231 | 0.0360 | 0.0390 |
| | 1.5 g/kg | 0.0220 | 0.0226 | 0.0172 |

Note:
The control group is the one administered with physiological saline, and the ethanol administration group is the one administered first with physiological saline and then with ethanol.

As can be seen from FIG. 1 and Table 1, the *Sophora flavescens* crude extract (KNA32) according to the present invention shows the equal or higher efficacy of decreasing the blood alcohol concentration in comparison to the commercially available drinks for alleviating hangover.

Experiment 2

Activity Assay of Glutamate-Oxaloacetate Transaminase (GOT)

In order to measure the efficacy of the *Sophora flavescens* crude extract obtained in <Example 1> on the decrease of blood GOT, 5 to 6 week-old (140 to 160 g of weight) male SD (Sprague Dawley) rats (Orientbio Inc., Seongnam, Korea) were used as test animals. The rats were fed ad libitum with solid feed and tap water for 1 week, and after this pre-breeding they were subjected to the test.

After 18 hours fast, the control group was orally administered with physiological saline and the test groups were orally administered with suspensions of the *Sophora flavescens* crude extract (KNA32) of <Example 1> in physiological saline in the concentrations of 0.5, 1.0 and 1.5 g/kg/5 ml, respectively. For the comparative groups 1 and 2, two kinds of commercially available drinks for alleviating hangover were selected (Comparative group 1: Heot-gae Condition Power, CJ Cheiljedang; Comparative group 2: Morning Care, Dong—A Pharmaceutical Co., Ltd). The rats of comparative groups were orally administered with these drinks of the selected dose which was calculated based on the recommended dose for the standard weight of an adult (70 kg) (dose concentration: 1.5 ml/kg for Heot-gae Condition Power and Morning Care) after being diluted in physiological saline (5 ml/kg).

Figure 2:
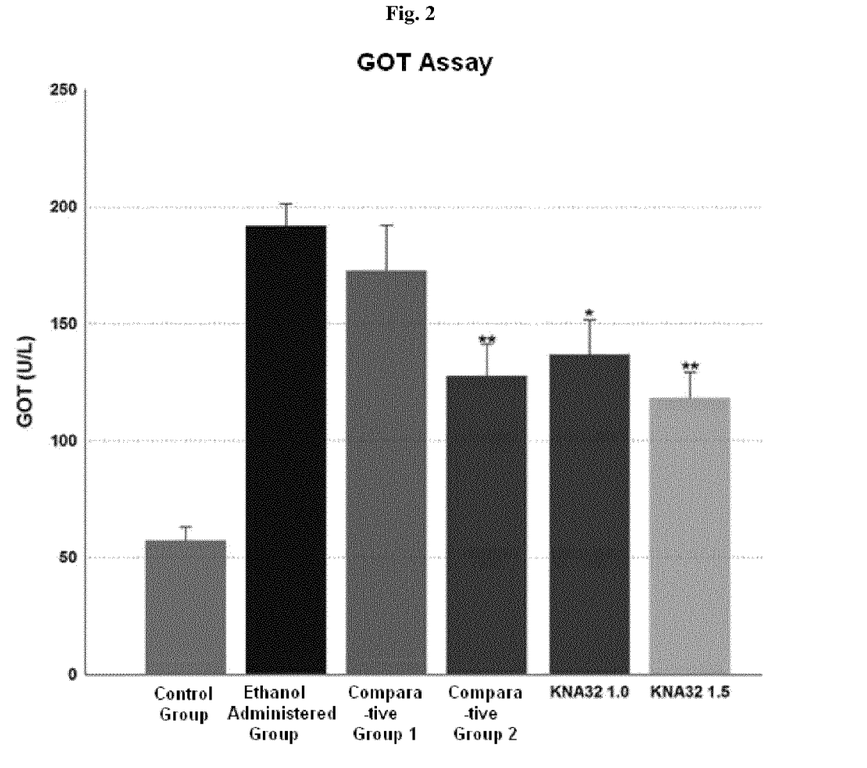
FIG. 2 represents a graph showing the change of blood GOT concentration after administering different doses of the *Sophora flavescens* crude extract according to one example (KNA32) to rats orally administered with alcohol in advance.

After 30 min, the rats of control group, test groups (administered with 0.5, 1.0 and 1.5 g/kg/5 ml of the *Sophora flavescens* crude extract) and comparative groups 1 and 2 were orally administered with alcohol in the concentration of 3 g/kg/10 ml. At 0.5, 2.5 and 4.5 h from the oral administration, blood was collected from the eye socket and heart. The collected blood was centrifuged for 10 min at 4° C., 10,000 rpm to separate the serum (sample serum). The GOT activity was measured by using a GOT assay kit (YD diagnostics, Yongin, Korea) for the test group serum of 4.5 h at which the value was highest in the preliminary experiment. In this measurement, the degradation rate of NADH measured by the absorbance at 340 nm was used as an indicator. 1 ml each of the reaction solution in the assay kit (NADH 0.22 mM, LDH 800 U/L, MDH 600 U/L, L-Aspartic acid 200 mM) and 0.1 ml each of the sample serum were introduced into a cuvette and reacted as a whole for 1 min at 37° C. The change of absorbance at 340 nm was measured for 1 min. The amount of GOT in each sample serum was obtained in the unit of U/L and is represented in FIG. 2 and Table 2.

TABLE 2

| Group | | Blood GOT Concentration (U/L) 4.5 h |
|---|---|---|
| Control Group | | 57.1653 |
| Ethanol Administration Group | | 191.7017 |
| Comparative Group 1 | | 172.7589 |
| Comparative Group 2 | | 127.5486 |
| KNA32 | 1.0 g/kg | 136.6411 |
| | 1.5 g/kg | 117.9509 |

Note:
The control group is the one administered with physiological saline, and the ethanol administration group is the one administered first with physiological saline and then with ethanol.

As can be seen from FIG. 2 and Table 2, the *Sophora flavescens* extract (KNA32) according to the present invention shows the equal or higher efficacy of inhibiting the increase of blood GOT in all concentrations administered in comparison to the commercially available drinks for alleviating hangover.

Experiment 3

Activity Assay of Alcohol Dehydrogenase (ADH)

In order to evaluate the effect of the *Sophora flavescens* fraction obtained in <Example 2> on the activation of alcohol dehydrogenase, 26.4 mg of the lyophilized S9 rat liver homogenate (MOLTOX Co., USA) was dissolved in 8 ml of 0.1% (w/v) BSA (bovine serum albumin) solution to the final concentration of 3.3 mg/ml and filtered through a 0.45 μm syringe filter to prepare the enzyme source.

The activity of alcohol dehydrogenase was assayed by using the production rate of NADH measured by the absorbance at 340 nm as an indicator. As the reaction solution, a mixture of distilled water 2.1 ml; 1.0 M Tris-HCl buffer (pH 8.0) 0.3 ml, 20 mM NAD$^+$ 0.1 ml, 1.0 M acetaldehyde 0.1 ml; 3.0 M KCl 0.1 ml; 0.33 M 2-mercaptoethanol 0.1 ml; 50 or 100 μg/ml the *Sophora flavescens* fraction (Example 2) 0.1 ml or the comparative sample (Morning Care, Dong—A Pharmaceutical Co., Ltd) 10 μl, and the enzyme source 0.1 ml were introduced into a cuvette. The volume was adjusted to a total of 3 ml and the reaction solution was reacted as a whole for 5 min at 30° C. The change of absorbance at 340 nm was measured for 5 min.

Figure 3:
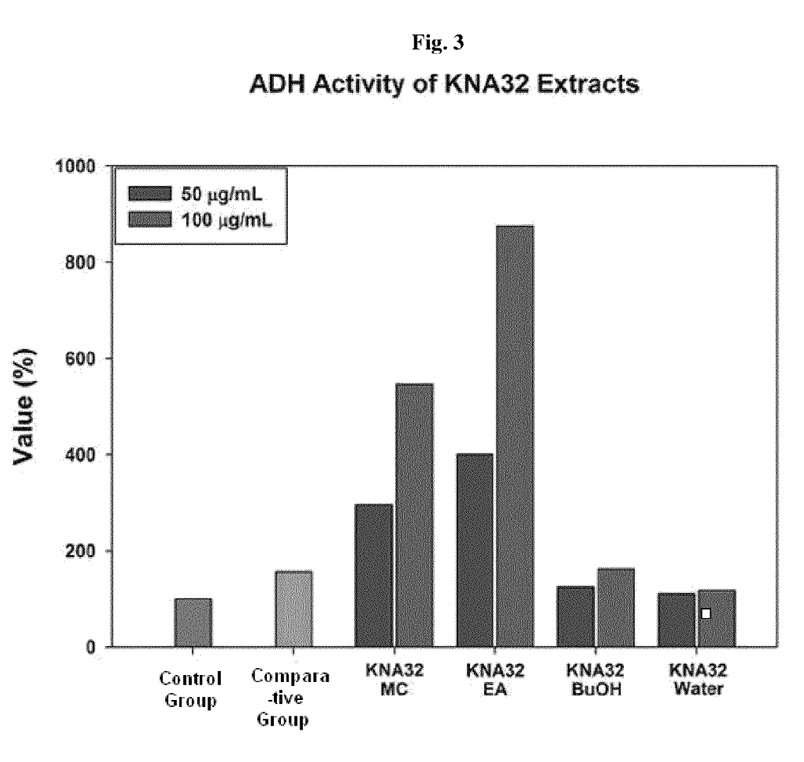
FIG. 3 represents a graph showing the activity change of alcohol dehydrogenase depending on the concentration of the *Sophora flavescens* crude extract according to one example (KNA32) added.

The control group was the one not administered with the *Sophora flavescens* fraction, and the comparative group was the one administered with the commercially available drink for alleviating hangover (Morning Care, Dong—A Pharmaceutical Co., Ltd). The alcohol dehydrogenase activities of the comparative group and the *Sophora flavescens* fraction were determined as the relative activity (%) with respect to that of the control group. The result of measurement is represented in FIG. 3 and Table 3.

TABLE 3

| Group | Activity of Alcohol Dehydrogenase (%) |
|---|---|
| Control Group | 100.0 |
| Comparative Group | 156.7 |

TABLE 3-continued

| Group | Activity of Alcohol Dehydrogenase (%) |
|---|---|
| (Morning Care) | |
| KNA32 MC 50 μg/ml | 296.0 |
| KNA32 MC 100 μg/ml | 546.4 |
| KNA32 EA 50 μg/ml | 400.5 |
| KNA32 EA 100 μg/ml | 875.8 |
| KNA32 BuOH 50 μg/ml | 124.9 |
| KNA32 BuOH 100 μg/ml | 162.6 |
| KNA32 Water 50 μg/ml | 111.2 |
| KNA32 Water 100 μg/ml | 118.4 |

As can be seen from FIG. 3 and Table 3, the ethyl acetate fraction (KNA32 EA) among the fractions prepared from the *Sophora flavescens* extract according to the present invention shows the most excellent effect in increasing the activity of alcohol dehydrogenase. The dichloromethane fraction (KNA32 MC) also shows the superior effect of activating the alcohol dehydrogenase.

Experiment 4

Activity Assay of Acetaldehyde Dehydrogenase (ALDH)

In order to measure the efficacy of the *Sophora flavescens* fraction obtained in <Example 2> on the activation of acetaldehyde dehydrogenase, 26.4 mg of the lyophilized S9 rat liver homogenate (MOLTOX Co., USA) was dissolved in 8 ml of 0.1% (w/v) BSA (bovine serum albumin) solution to the final concentration of 3.3 mg/ml and filtered through a 0.45 μm syringe filter to prepare the enzyme source.

Figure 4:
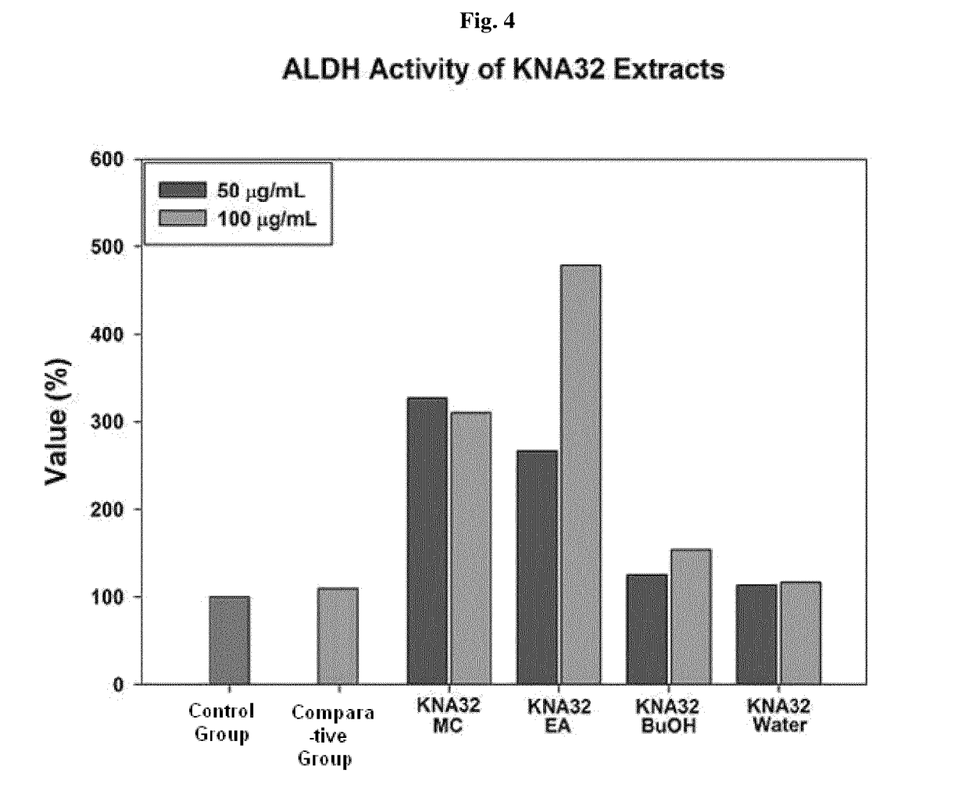
FIG. 4 represents a graph showing the activity change of acetaldehyde dehydrogenase depending on the concentration of the *Sophora flavescens* crude extract according to one example (KNA32) added.

The activity of acetaldehyde dehydrogenase was assayed by using the production rate of NADH measured by the absorbance at 340 nm as an indicator. As the reaction solution, a mixture of distilled water 2.1 ml; 1.0 M Tris-HCl buffer (pH 8.0) 0.3 ml, 20 mM NAD$^+$ 0.1 ml, 1.0 M acetaldehyde 0.1 ml; 3.0 M KCl 0.1 ml; 0.33 M 2-mercaptoethanol 0.1 ml; 50 and 100 μg/ml the *Sophora flavescens* fraction (Example 2) 0.1 ml or 10 μl/ml the comparative sample (Morning Care, Dong—A Pharmaceutical Co., Ltd), and the enzyme source 0.1 ml were introduced into a cuvette. The volume was adjusted to a total of 3 ml and the reaction solution was reacted as a whole for 5 min at 30° C. The change of absorbance at 340 nm was measured for 5 min. Here, the control group was the one not administered with the sample, and the comparative group was the one administered with the commercially available drink for alleviating hangover (Morning Care, Dong—A Pharmaceutical Co., Ltd). The acetaldehyde dehydrogenase activity of the sample was determined as the relative activity (%) with respect to that of the control group. The result of measurement is represented in FIG. 4 and Table 4.

TABLE 4

| Group | Activity of Acetaldehyde Dehydrogenase (%) |
|---|---|
| Control Group | 100.0 |
| Comparative Group (Morning Care) | 109.7 |
| KNA32 MC 50 μg/ml | 327.4 |
| KNA32 MC 100 μg/ml | 310.2 |
| KNA32 EA 50 μg/ml | 266.7 |
| KNA32 EA 100 μg/ml | 478.4 |
| KNA32 BuOH 50 μg/ml | 125.3 |

TABLE 4-continued

| Group | Activity of Acetaldehyde Dehydrogenase (%) |
|---|---|
| KNA32 BuOH 100 µg/ml | 153.5 |
| KNA32 Water 50 µg/ml | 113.6 |
| KNA32 Water 100 µg/ml | 116.5 |

As can be seen from FIG. 4 and Table 4, the ethyl acetate fraction (KNA32 EA) among the fractions prepared from the *Sophora flavescens* extract shows the most excellent effect in activating the acetaldehyde dehydrogenase. The dichloromethane fraction (KNA32 MC) also effectively increase the activity of acetaldehyde dehydrogenase.

Experiment 5

Measurement of Inhibitory Efficacy on Deterioration of Exercise Capacity in Mice Administered with Ethanol In order to measure the inhibitory efficacy of the *Sophora flavescens* crude extract obtained in <Example 1> on the deterioration of exercise capacity, 11 week-old male C57BL/6 mice (Japan SLC Inc., Shizuoka, Japan) were used as test animals. The mice were fed ad libitum with solid feed and tap water for 1 week, and after this pre-breeding they were subjected to the test.

After 18 hours fast, the normal and control groups were orally administered with 1% (w/v) CMC-Na (Sodium carboxymethylcellulose, Sigma, USA) solution and the test groups were orally administered with suspensions of the *Sophora flavescens* crude extract (KNA32) of <Example 1> in 1% (w/v) CMC-Na solution in the concentrations of 150 mg/kg/10 ml and 300 mg/kg/10 ml, respectively. For the comparative group, the commercially available drink for alleviating hangover (Morning Care, Dong—A Pharmaceutical Co., Ltd) was selected, diluted in 1% (w/v) CMC-Na solution, and orally administered in the dose which was calculated based on the recommended dose for the standard weight of an adult (70 kg) (dose concentration: Morning Care 1.5 ml/kg).

Figure 5:
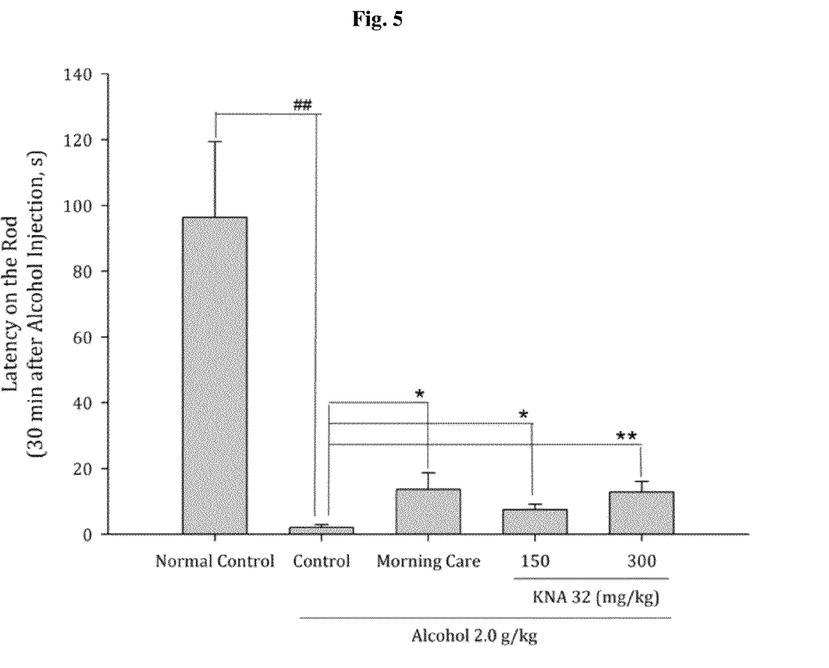
FIG. 5 represents a graph showing the dose-dependent efficiency of the *Sophora flavescens* crude extract according to one example (KNA32) on the deterioration of exercise capacity induced by the intraperitoneal administration of alcohol, after the crude extract is orally administered.

After 1 h, the mice of control group, comparative group and test groups (administered with 150 and 300 mg/kg/10 ml of the *Sophora flavescens* crude extract) were peritoneally administered with alcohol in the concentration of 2 g/kg/10 ml. After 30 min, the mice were placed on a rotarod instrument (16 rpm, fixed) that can measure the exercise capacity to obtain the time required fill the loss of exercise capacity. The result is shown in FIG. 5. As can be seen from FIG. 5, the *Sophora flavescens* crude extract (KNA32) significantly inhibits the deterioration of exercise capacity due to the alcohol ingestion.

Experiment 6

Measurement of Sleep-Wake Efficacy in Mice Administered with Ethanol

In order to measure the sleep-wake efficacy of the *Sophora flavescens* crude extract obtained in <Example 1>, 11 week-old male C57BL/6 mice (Japan SLC Inc., Shizuoka, Japan) were used as test animals. The mice were fed ad libitum with solid feed and tap water for 1 week, and after this pre-breeding they were subjected to the test.

After 18 hours fast, the control group was orally administered with 1% (w/v) CMC-Na (Sodium carboxymethylcellulose, Sigma, USA) solution and the test groups were orally administered with suspensions of the *Sophora flavescens* crude extract (KNA32) of <Example 1> in 1% (w/v) CMC-Na solution in the concentrations of 150 mg/kg/10 ml and 300 mg/kg/10 ml, respectively. For the comparative group, the commercially available drink for alleviating hangover (Morning Care, Dong—A Pharmaceutical Co., Ltd) was selected, diluted in 1% (w/v) CMC-Na solution, and orally administered in the dose which was calculated based on the recommended dose for the standard weight of an adult (70 kg) (dose concentration: Morning Care 1.5 ml/kg).

Figure 6:
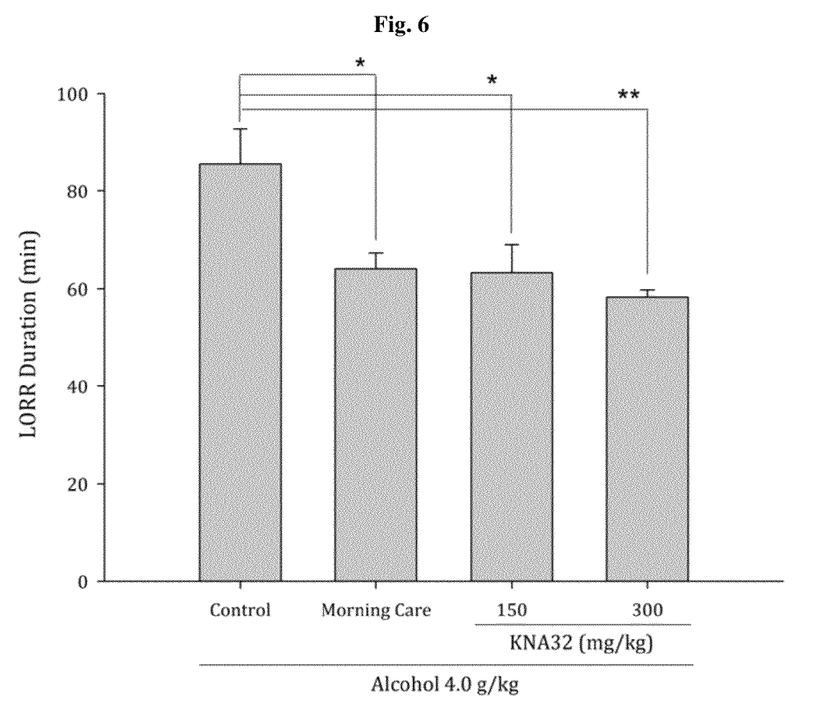
FIG. 6 represents a graph showing the dose-dependent efficiency of the *Sophora flavescens* crude extract according to one example (KNA32) on the sleep-wake induced by the intraperitoneal administration of alcohol, after the crude extract is orally administered.

After 1 h, the mice of control group, comparative group and test groups (administered with 150 and 300 mg/kg/10 ml of the *Sophora flavescens* crude extract) were peritoneally administered with alcohol in the concentration of 4 g/kg/10 ml. To determine the sleep-wake of the mice which went on sleep due to the alcohol administration, LORR Method (Loss of righting reflex test) was used. The mice in sleep were laid down in a breeding cage of which bottom was covered with bedstraws with their limbs upward, and the time needed for them to have the correct posture with their limbs downward after they were wakened from the sleep was measured. The result is shown in FIG. 6. As can be confirmed from FIG. 6, the *Sophora flavescens* crude extract (KNA32) according to the present invention shows the significant effect in waking sleep due to the alcohol ingestion, and in particular the test group administered with 300 mg/kg shows the more improved efficacy than the commercially available drink.

What is claimed is:

1. A method of alleviating alcohol hangover, comprising administering one or more selected from the group consisting of *Sophora flavescens* extract, dried products of the *Sophora flavescens* extract, and concentrates of the *Sophora flavescens* extract to a subject in need of alleviating alcohol hangover,
wherein the *Sophora flavescens* extract is at least a *Sophora flavescens* crude extract obtained by extracting *Sophora flavescens* using (i) one or more extraction solvents selected from the group consisting of straight-chain or branched $C_1$-$C_4$-alcohol, dichloromethane, ethyl acetate and acetone, or (ii) a mixture of water and one or more extraction solvents selected from the group consisting of straight-chain or branched $C_1$-$C_4$-alcohol, dichloromethane, ethyl acetate and acetone; and
a *Sophora flavescens* fraction obtained through the solvent fractionation by adding one or more fractionation solvents selected from the group consisting of hexane, chloroform, ether, dichloromethane, ethyl acetate, butanol and water to the *Sophora flavescens* crude extract.

2. The method according to claim 1, wherein the *Sophora flavescens* fraction is one or more selected from the group consisting of:
a fraction obtained by suspending the *Sophora flavescens* crude extract in water, to produce a suspension of the *Sophora flavescens* crude extract, and adding one or more fractionation solvents selected from the group consisting of hexane, chloroform, ether, dichloromethane, ethyl acetate and butanol in the same volume as water to the suspension, to fractionate the suspension; and
a fraction obtained by adding one or more fractionation solvents selected from the group consisting of hexane, chloroform, ether, dichloromethane, ethyl acetate, butanol and water to the *Sophora flavescens* crude extract, to fractionate the crude extract.

3. The method according to claim 1, wherein one or more selected from the group consisting of the *Sophora flavescens* extract, the dried products of the *Sophora flavescens* extract, and the concentrates of the *Sophora flavescens* extract are formulated as a drink, wherein the drink is free from one or more materials selected from the group consisting of black tea, kudzuvine root, galangal, chrysanthemum, lablab bean, nutmeg, fructus aurantii immaturus, tsaoko amomum fruit, licorice, hawthorn, herba periliae, loranthus mulberry mistletoe, lilac, honeysuckle flower, cogongrass rhizome, tangerine peel and mint.

4. The method according to claim 1, wherein the *Sophora flavescens* crude extract is obtained by extracting *Sophora flavescens* using a solvent mixture of water and at least one selected from the group consisting of a straight-chain or branched $C_1$-$C_4$-alcohol in the mixing ratio of 1:9 to 5:5 by volume.

5. The method according to claim 1, wherein one or more selected from the group consisting of the *Sophora flavescens* extract, the dried products of the *Sophora flavescens* extract, and the concentrates of the *Sophora flavescens* extract are formulated as a pharmaceutical composition or a food composition.

6. The method according to claim 5, wherein the pharmaceutical composition may comprise one or more materials selected from the group consisting of a carrier, excipient and diluent.

\* \* \* \* \*